United States Patent
Tjugum

(10) Patent No.: US 7,978,815 B2
(45) Date of Patent: Jul. 12, 2011

(54) COMPACT GAMMAMETER

(75) Inventor: Stein-Arild Tjugum, Laksevåg (NO)

(73) Assignee: Roxar Flow Measurement AS, Bergen (NO)

( * ) Notice: Subject to any disclaimer, the term of this patent is extended or adjusted under 35 U.S.C. 154(b) by 89 days.

(21) Appl. No.: 12/377,311

(22) PCT Filed: Aug. 28, 2007

(86) PCT No.: PCT/NO2007/000303
§ 371 (c)(1),
(2), (4) Date: Feb. 12, 2009

(87) PCT Pub. No.: WO2008/026935
PCT Pub. Date: Mar. 6, 2008

(65) Prior Publication Data
US 2010/0065730 A1    Mar. 18, 2010

(30) Foreign Application Priority Data
Aug. 29, 2006 (NO) .................................. 2006 3846

(51) Int. Cl.
*G01B 15/02* (2006.01)
(52) U.S. Cl. ....................................................... 378/54
(58) Field of Classification Search .............. 378/51, 378/47, 50, 54, 57, 58, 89, 90, 119
See application file for complete search history.

(56) References Cited

U.S. PATENT DOCUMENTS

| 4,282,433 | A | * | 8/1981 | Loffel ........................ 250/356.1 |
| 4,352,288 | A | * | 10/1982 | Paap et al. .................... 73/61.41 |
| 4,795,903 | A | | 1/1989 | Clayton |
| 6,265,713 | B1 | | 7/2001 | Berard et al. |

FOREIGN PATENT DOCUMENTS

| EP | 0 269 432 | 6/1988 |
| GB | 2 325 735 | 12/1998 |
| WO | WO 97/29356 | 8/1997 |
| WO | WO 01/25762 | 4/2001 |
| WO | WO 02/35059 | 5/2002 |
| WO | WO 03/021234 | 3/2003 |
| WO | WO 2006/067525 | 6/2006 |

OTHER PUBLICATIONS

International Search Report for PCT/N02007/000303, mailed Nov. 22, 2007.
International Preliminary Report on Patentability for PCT/NO2007/000303, dated Jun. 30, 2008.
Norwegian Search Report for Norway Application No. 20063846, dated Mar. 7, 2007.

* cited by examiner

*Primary Examiner* — Irakli Kiknadze
(74) *Attorney, Agent, or Firm* — Nixon & Vanderhye PC

(57) ABSTRACT

This invention relates to a compact density measuring instrument for measuring density of fluids in a volume in a container, especially in a fluid flow in a pipe, the instrument comprising a radiation source in the gamma range positioned on one side of the fluid and a detector positioned on the opposite side of the fluids for receiving said radiation, and the fluid being contained in the container, wherein the source is positioned in a source housing, said source housing being at least partially fitted into a corresponding recess in the container wall, said source housing comprises a source holder containing the gamma source positioned in the holder axis and comprising a coaxial opening from the source through one end of the holder, said one end adapted to be aimed toward the fluid.

20 Claims, 2 Drawing Sheets

COMPACT GAMMAMETER

This application is the U.S. national phase of International Application No. PCT/NO2007/00303, filed 28 Aug. 2007, which designated the U.S. and claims priority to Norway Application No. 2006 3846, filed 29 Aug. 2006, the entire contents of each of which are hereby incorporated by reference.

This invention relates to a gamma-ray flow measuring instrument for measuring the density of a fluid in a volume in a container, especially in a fluid flow in a pipe or similar. More specific the invention relates to a construction where a source and detector are partially inserted into the pipe wall and the pipe opening area has a conical shape so as to reduce the vulnerability of the pipe wall and at the same time let the source come as close as possible to the detector.

In oil and gas production it is important to monitor the quality and composition of the production flow, and among these the density of the fluid flow, where the fluid may comprise both gas and liquids like oil and water. For density measurements gamma sources are often used. These are based on positioning a gamma source and detector on opposite sides of the flow and measuring the differences in detector signal depending on the density of the flow. The present systems often require the use of high activity gamma sources of the Cs137 type in the range of 1100-1900 kBq (30-50 mCurie) and energies in the range of 660 keV, and thus requires special handling of radioactive materials in addition to constituting large units to be mounted on the pipe.

The object of the present invention is to provide a more compact solution which provides sufficiently good measurements and also requires gamma sources with lower activity. This is obtained with an instrument as specified in the independent claims.

In the solution according to the invention the gamma source is inserted into a recess in the pipe wall corresponding to the outer shape of the source housing. Depending of the photon energy generated by the source the source housing may be constituted by an outer lead filled steel housing or titanium housing with a tungsten or steel core or source holder including the gamma source preferably positioned coaxially therein. The core or holder also includes a channel from the embedded gamma point source toward the pipe centre. Coaxial with the core and channel a conical protrusion is provided surrounding an extension of the channel and forming a point into a corresponding cavity in the centre of the recess in the pipe wall.

This leaves a relatively short propagation path through the pipe material before entering the flow, which results on low attenuation in the pipe material and also avoids weakening the pipe more than necessary. In addition a sufficiently concentrated beam through the flow and to the detector is obtained.

According to one embodiment of the invention for measuring density of multiphase flows the recess is made into the pipe wall leaving a part of the pipe wall between the top of the core and the flow. In this case the source emits relatively high energy radiation, e.g. a Cs137 source, which results in a requirement for the source housing to provide a good shielding, e.g. being made from lead or a lead filled steel casing with a tungsten core.

According to another embodiment of the invention, especially related to measurements in wet gas flows the line between the source and detector has an angle relative to the flow axis. This is advantageous because a longer propagation path provides improved measurement sensitivity as the wet gas otherwise has too low attenuation at the relevant photon energies. In these cases an Am241 source may be placed in a steel core and e.g. having titanium housing, and the pipe wall is replaced by a portion of e.g. a PEEK material low attenuation of the gamma radiation and also being capable of withstanding the conditions in the flow.

In the other side of the pipe a detector is inserted in a suitable recess, preferably having a cavity in front of the detector with a smaller diameter to reduce the material thickness of the pipe directly between the detector and the flow.

The invention will be described below with reference to the accompanying drawings, illustrating the invention by way of examples.

Figure 1:
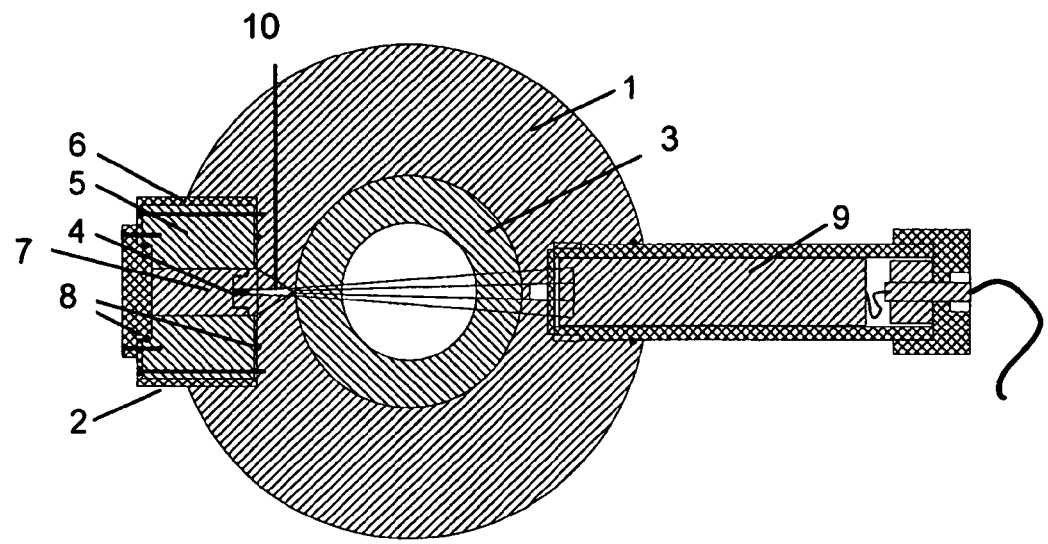
FIG. 1 illustrates an embodiment of the invention adapted for the use with a Cs137 source in a multiphase flow.

FIG. 1 illustrates a gamma instrument mounted in a pipe 1. The pipe 1 is made from steel and in addition the illustrated pipe comprises a PEEK (polyetheretherketone) material 3 on its inner surface. The latter may be required if the gamma instrument is combined with other measuring instruments, e.g. with electrodes in contact with the flow, but is not important to the present invention. PEEK is often used in relation to multiphase hydrocarbon flows because of its mechanical durability, and chemical neutrality in combination with the components in the flow in varying temperatures.

As is seen in FIG. 1 a gamma source housing 2 is positioned in a recess in the pipe wall and being fastened therein by any available means. The housing and recess is also sealed O-rings 8 to avoid leaks through the recess. According to the preferred embodiment for measurements in multiphase fluids comprising a Cs137 source the housing 5 is preferably made from a high density material like lead, but in some cases, e.g. when using less active gamma sources, steel may be used. In the illustrated example a lead filled 5 steel housing 6 is shown. The source 4 is positioned in a core or source holder 7 positioned coaxially in the housing, and this core has a channel from the source toward the flow inside the pipe. Depending on the source material the core may be of different types of relatively high density materials but in the illustrated example the core is made from Tungsten or other absorbing materials, and with less active sources a combination of steel housing and enlarged Tungsten core may be used.

Figure 4:
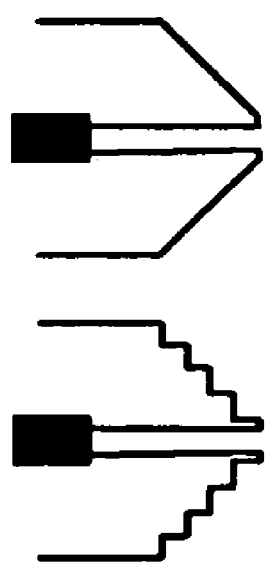
FIG. 4 illustrates a possible variation in the essentially conical shape of the source holder.

In order to reduce the gamma-ray attenuation in the pipe material it is advantageous that the thickness through the material is as small as possible, but without weakening the pipe wall. This is obtained by providing an essentially conically shaped tip 10 on the core which protrudes into the pipe wall wherein the channel in the core extends through the cone and out from the tip. This conical shape provides a sharp beam cross section as it provides a long channel through the absorbing material, but does not weaken the wall in the same degree as would be the case if the core had the same cross section along its length. The essentially conical shape of the tip 10 may in practice deviate from the smooth cone, e.g. due to machining considerations, for example in a stepwise reduction of the radius toward the end of the tip, as is illustrated in FIG. 4.

In the drawing approximately 5 mm of pipe material remain in front of the core channel. This reduces the requirements for source strength and thus may reduce the problems related to handling of radioactive sources in density measuring instruments. As stated above the preferred source 4 in this embodiment is a Cs 137 source, preferably in the range of $3.7\text{-}37\times10^7$ Becquerel (1-10 mCurie), especially $18.5\times10^7$ Becquerel (5 mCurie).

Figure 3:
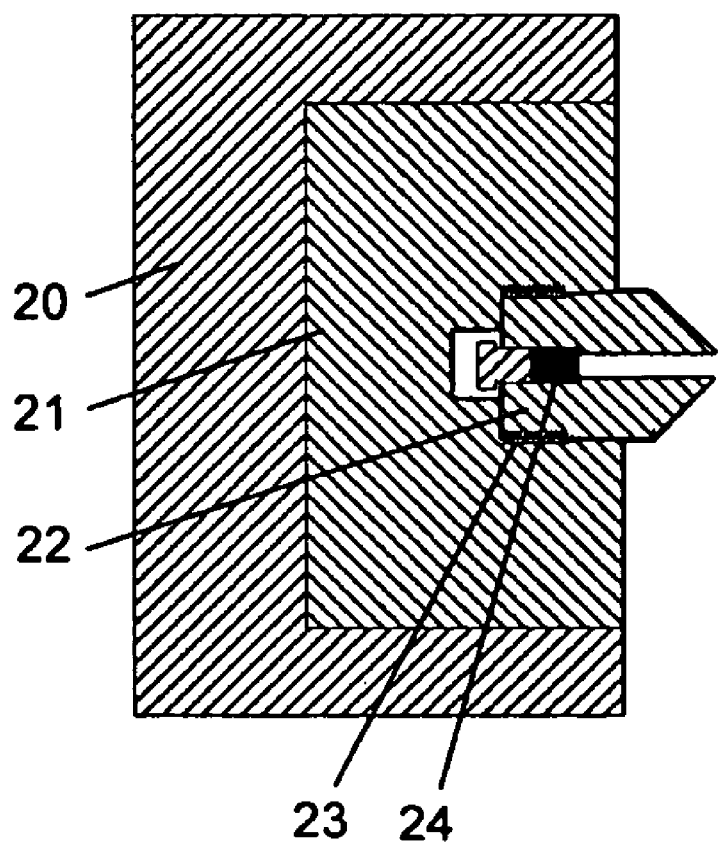
FIG. 3 illustrates an alternative embodiment of the source housing and holder.

FIG. 3 illustrates an alternative embodiment of the source housing and core, where the housing 2 is provided as a steel shell 20 enclosing a Tungsten inner part 21, and in which the core/source holder 22 is also made from Tungsten. The core 22 is mounted into the inner part 21 by a threaded coupling 23, and the source 24 is incorporated in the source holder 22.

As with the source housing the detector 9, which may be on any suitable type, is positioned in a recess in the pipe wall on the other side of the flow. With the Cs 137 source the energy being detected is in the range of range ~660 eV, as lower energies from the source will be absorbed by the steel in the pipe wall.

In the illustrated embodiment a cavity is also provided in front of the detector 9 to reduce the wall thickness in front of the detector, thus to reduce the attenuation in front of the detector. In this case the pipe wall in front of the detector and the source is approximately 5 mm, but this may be chosen according to the specific use of the instrument.

In FIG. 1 the detector is positioned on the opposite side of the flow relative to the source. The detector may also be provided with a frustoconical shape in order to reduce the weakening of the pipe wall. Other configurations may be contemplated, such as several detectors positioned off the beam axis for detecting radiation scattered from the flow, as discussed in Norwegian patent application No. 1999.2988 for the purpose of obtaining salinity independent density measurement in the flow.

According to another embodiment of the invention the radiation may be transmitted directly from the one or more sources through different parts of the flow. This way it will be possible to provide measurements of the density on the flow centre as well as close to the pipe wall, so as to make it possible to detect a layered structure where different fluids are found at different distances from the flow centre.

A radiation beam aimed at measuring close to pipe wall will both leave and enter the pipe wall at an angle. In high pressure environments the detector and source housing has to be positioned at a distance from the inner pipe wall so as not to weaken the wall. When the beam has to leave the wall at an angle this also means that it in these cases has to propagate through more pipe wall material before entering the flow. In order to avoid this, a cavity may be provided into the inner pipe wall so as to reduce the propagation length through the pipe wall, and this cavity may be filled with a material being relatively transparent to the radiation, e.g. PEEK material. A related solution is illustrated in FIG. 2, where the beam has an angle relative to the flow direction and the pipe wall.

Figure 2:
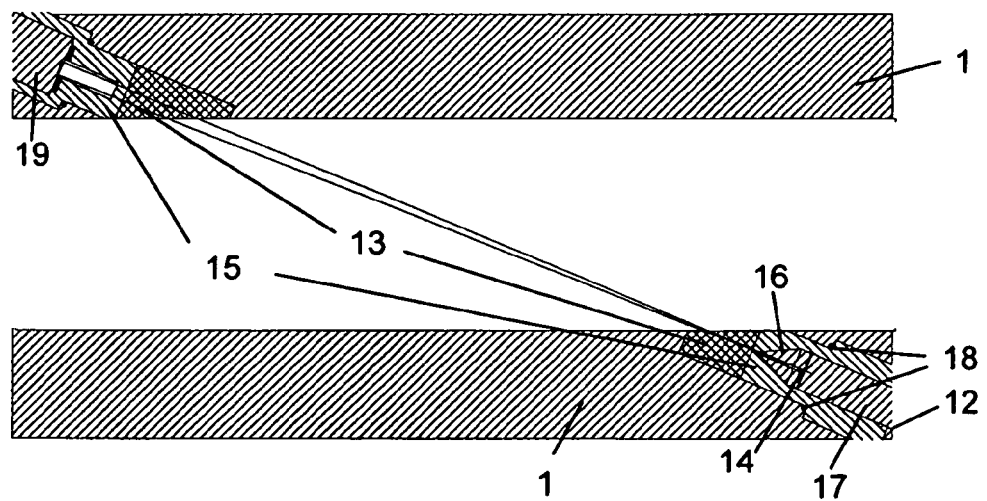
FIG. 2 illustrates an embodiment of the invention adapted for the use with a Am241 source in a wet gas flow.

As illustrated in FIG. 2 the gamma beam may also be aimed at an angle relative to the flow. This is especially suitable when measuring the density of wet gas flows, where the fluid has a low attenuation rate and the sensitivity may be increased by increasing the propagation length through the fluid flow. The angle will depend on the attenuation in the flow and sensitivity of the detector relative to the beam energy, but will usually be below 75 degrees so as to obtain a significant increase in the beam path length.

In the embodiment illustrated in FIG. 2 a source 14 with lower energy may be used, such as Am241, thus requiring a reduced wall thickness to avoid too much attenuation in the steel pipe walls 11. As is illustrated this is solved by constructing the recess by making a hole through the pipe wall and positioning the source housing in the outer parts of this opening, and sealing it for avoiding leaks though the opening in any suitable way being available for a person skilled in the art, e.g. by using O-rings as illustrated in the drawings. Also, because of the angle against the pipe wall and the required thin metal in front of the source housing a recess is left in the inner pipe wall. In order to avoid turbulence and materials deposited in the recess a window 13 for the gamma radiation, e.g. made from PEEK or similar materials, is position in the recess. In contrast to the embodiment illustrated in FIG. 1 the source housing 12 is made from an outer casing 15 of a low density materials such as titanium alloys with a steel core 17 containing the source 14. As in the first embodiment the core protrudes with a conical shape 16 toward the flow, but in this case the housing 12 covers the tip of the cone and provides a wall for the gamma rays in the outer end of the channel closest to the flow, so as to protect the source from interactions with leaks etc from the flow passing the peek material 13. In the preferred embodiment of this solution the housing 12 may have a thickness of 5 mm on front of the cone 16. Titanium alloys are especially advantageous in this application as it combines mechanical strength with low attenuation, thus acting as a window for the radiation in front of the cone opening. This could also be solved with a thin steel plate in the end of the channel, at the cost of mechanical strength or increased absorption.

According to the embodiment illustrated in FIG. 2 adapted for performing measurements in wet gas flows an Am241 source in the range of $180\text{-}1100\times10^7$ Becquerel (50-300 mCurie) is used and a detector 19 suitable for detecting in the energy range of ~59.5 keV is preferred.

Because of the low energies a solution similar to the solution related to the source is used in relation to the detector, with a radiation window made from PEEK or similar materials is used between the detector and the fluid flow.

The embodiments disclosed in FIGS. 1 and 2 are suitable for different applications. The compact gamma density measuring instrument illustrated in FIG. 1 represents the preferred embodiment in situations where the flow is a multiphase flow comprising e.g. oil, water and gas. In this case the source and detector is positioned directly opposite each other with a beam having a 90° angle relative to the fluid flow direction.

The gamma density measuring instrument in FIG. 2 represents a preferred embodiment in the case where the flow is constituted by wet gas, i.e. mainly gas with some contributions of water and/or oil.

In both situations the invention is aimed at providing a compact solution providing good dynamical range of measurements performed without using strong gamma sources.

Although this invention is mainly adapted to measurements in pipes containing fluid flows passing the measuring instrument it may also be used for containers containing fluids, e.g. for measuring the density of a pressurized fluid inside a tank.

The invention claimed is:

1. Compact density measuring instrument for measuring density of fluids in a volume in a container, especially in a fluid flow in a pipe, the instrument comprising a radiation source in the gamma range positioned on one side of the fluid and a detector positioned on the opposite side of the fluid for receiving said radiation, and the fluid being contained in the container, wherein the source is positioned in a source housing, said source housing being at least partially fitted into a corresponding recess in the container wall, said source housing comprises a source holder containing the gamma source positioned in the holder axis and comprising a coaxial opening from the source through one end of the holder, said one end adapted to be aimed toward the fluid, wherein the outer part of said one end of the source holder has an essentially conical shape with decreasing radius toward the fluid and being adapted to fitted into a corresponding cavity in the container wall and wherein the recess and cavity together have a depth less than the thickness of the container wall, thus leaving a part of the container wall between the tip of the cone and the fluid.

2. Instrument according to claim 1, wherein the detector is positioned in a detector housing being fitted into a corresponding recess in the container on the opposite side of the fluid relative to the source.

3. Instrument according to claim 1, wherein the source holder is made from a relatively high density material.

4. Instrument according to claim 3, wherein the source holder is made from tungsten.

5. Instrument according to claim 1, wherein said source holder is coaxially mounted in a high density material housing, said housing being adapted to be fastened to the container.

6. Instrument according to claim 5, wherein the high density material housing is made from lead.

7. Instrument according to claim 1, wherein the container is a pipe part adapted to be mounted in a pipe line.

8. Instrument according to claim 1, wherein the source is a Cs-137 gamma source.

9. Instrument according to claim 1, wherein the source and detector are positioned in the walls of a pipe, wherein the beam axis between the source and the detector has an angle relative to the pipe axis being less than 90 degrees, the source being positioned in a hole in the pipe wall and a material being transparent for the gamma radiation being positioned between the source and the continuation of the inner surface of the pipe wall.

10. Instrument according to claim 9, wherein the source is positioned in a housing also comprising a metal source holder containing the gamma source positioned in the holder axis and a coaxial opening from the source through one end of the rod, said one end adapted to be aimed toward the fluid.

11. Instrument according to claim 10, wherein said source housing is made from low density material.

12. Instrument according to claim 11, wherein the low density material is a titanium alloy.

13. Instrument according to claim 10, wherein the housing covers the outer end of the holder channel through the holder.

14. Instrument according to claim 13, wherein the thickness of the housing in front of the holder end is in the range of 1-7 mm.

15. Instrument according to claim 10, wherein the metal source holder is made from steel.

16. Instrument according to claim 9, wherein the detector is contained in a detector housing being fitted into a corresponding recess in the pipe wall on the opposite side from the source.

17. Instrument according to claim 9, wherein the source is a low energy gamma source.

18. Instrument according to claim 17, wherein the low energy gamma source is Am-241.

19. Instrument according to claim 9, wherein said detector is also positioned in an opening in the pipe wall and has a front part being retreated from inner pipe surface, and a material being essentially transparent to the gamma radiation being positioned between the housing and the inner pipe surface, the transparent material thus representing an essentially seamless continuation of the pipe surface.

20. Instrument according to claim 19, wherein the transparent material is polyether ether ketone (PEEK).

* * * * *